United States Patent [19]

Chaiet et al.

[11] 4,007,090

[45] Feb. 8, 1977

[54] NOVEL FERMENTATION PROCESS FOR THE PREPARATION OF SULFOMYCIN

[75] Inventors: Louis Chaiet, Springfield, N.J.;
Sebastian Hernandez, Madrid, Spain;
Sheldon B. Zimmerman, Springfield, N.J.

[73] Assignee: Merck & Co., Inc., Rahway, N.J.

[22] Filed: Apr. 2, 1976

[21] Appl. No.: 673,039

[52] U.S. Cl. .............................................. 195/80 R
[51] Int. Cl.² ......................................... C12D 9/00
[58] Field of Search ................................. 195/80 R

[56] References Cited

FOREIGN PATENTS OR APPLICATIONS 45-6880   3/1970   Japan .............................. 195/80 R
17,599    6/1970   Japan

OTHER PUBLICATIONS

Egawa et al., The Journal of Antibiotics, vol. 22, No. 1, 1969, pp. 12–17.

*Primary Examiner*—A. Louis Monacell
*Assistant Examiner*—Robert J. Warden
*Attorney, Agent, or Firm*—David L. Rose; J. Jerome Behan

[57] ABSTRACT

This invention relates to a novel process for the preparation of the antibiotic Sulfomycin. The antibiotic is obtained by the fermentation of a nutrient medium with a Sulfomycin producing strain of the previously unknown microorganism *Streptomyces cineroviridis*.

9 Claims, No Drawings

NOVEL FERMENTATION PROCESS FOR THE PREPARATION OF SULFOMYCIN

DESCRIPTION OF THE PRIOR ART

Sulfomycin I is a known gram-positive antibiotic described in Japan Pat. No. 45-6880. Sulfomycin II and III are also described in the literature as gram-positive antibiotics in Japan Pat. publication No. 17599/1970. All three Sulfomycin antibiotics were prepared by the fermentation of a strain of the microorganism *Streptomyces viridochromogenes*. The antibiotics were isolated from the culture fluid and from within the cells.

SUMMARY OF THE INVENTION

The instant invention is concerned with a novel preparation of the antibiotic Sulfomycin I. The process involves isolation of the antibiotic from the fermentation broth *Streptomyces cineroviridis*. Thus, it is an object of this invention to describe the preparation, through fermentation, of Sulfomycin. Further objects will become apparent from a reading of the following Description of the Invention.

DESCRIPTION OF THE INVENTION

The antibiotic substance Sulfomycin is prepared in the present invention, by growing, under controlled conditions, a previously unknown strain of the microorganism *Streptomyces cineroviridis*. The *Streptomyces cineroviridis* microorganism was isolated from a sample of soil from Beirut, Lebanon. A culture has been deposited without restriction as to availability with the Fermentation Section of the Northern Utilization Research Branch, U.S. Department of Agriculture at Peoria, Ill. and is added to the permanent culture collection, and is available to the public under culture No. NRRL 8155.

The morphological and cultural characteristics of *Streptomyces cineroviridis* are set forth in the following Table:

Morphology:

Sporophores are compact spirals occuring as short side branches on aerial mycelium. Spores are spherical, $0.9\mu$ in diameter. Spore surface is smooth as observed on yeast extract malt extract agar at 9500 X.

Cultural Characteristics

Oatmeal agar
    Vegetative Growth: Reverse - light brown
    Aerial Mycelium: Moderate, grayish
    Soluble Pigment: Light brown Czapek Dox agar (sucrose nitrate agar)
    Vegetative Growth: Reverse - light brown
    Aerial Mycelium: Sparse - grayish
    Soluble Pigment: Light brown Egg albumin agar
    Vegetative Growth: Reverse - Tan
    Aerial Mycelium: Moderate - grayish white
    Soluble Pigment: Light brown Glycerol asparagine agar
    Vegetative Growth: Reverse - Tan
    Aerial Mycelium: Moderate - very pale cream with a grayed green tone.
    Soluble Pigment: Light brown Inorganic salts-starch agar
    Vegetative Growth: Reverse - Grayed tan
    Aerial Mycelium: Dark grayish green (24ih) with areas of grayed aqua (19dc)
    Soluble Pigment: Light grayish brown Yeast extract-dextrose + salts agar
    Vegetative Growth: Reverse - dark brown
    Aerial Mycelium: Pale gray with greenish tones
    Soluble Pigment: Brown Yeast extract-malt extract agar
    Vegetative Growth: Reverse - brown
    Aerial Mycelium: Dark grayish green (24ih) with areas of grayed aqua (19dc)
    Soluble Pigment: Brown Peptone-iron-yeast extract agar
    Vegetative Growth: Very dark brown
    Aerial Mycelium: None
    Soluble Pigment: Very dark brown - almost black
    Melanin: Positive
    $H_2S$ production: Positive Nutrient agar
    Vegetative Growth: Reverse - dark tan
    Aerial Mycelium: Grayed green (a pale tone of 24ih)
    Soluble Pigment: Brown Nutrient starch agar
    Vegetative Growth: Reverse - dark tan
    Aerial Mycelium: Grayed green (24ih)
    Soluble Pigment: Brown
    Hydrolysis of starch: Good Nutrient gelatin agar -continued

| | | |
|---|---|---|
| | Vegetative Growth: | Reverse - dark tan |
| | Aerial Mycelium: | Pale grayed green |
| | Soluble Pigment: | Brown |
| | Liquefaction of gelatin: | Good |
| Gelatin stabs | | |
| | Vegetative Growth: | Tan |
| | Aerial Mycelium: | None |
| | Soluble Pigment: | Dark brown |
| | Liquefaction of gelatin: | Moderate |
| Skim milk agar | | |
| | Vegetative Growth: | Brown |
| | Aerial Mycelium: | None |
| | Soluble Pigment: | Brown |
| | Hydrolysis of casein: | Good |
| Litmus milk | | |
| | Vegetative Growth: | Tan growth ring |
| | Aerial Mycelium: | None |
| | Color: | Brown |
| | Coagulation and/or peptonization: | Peptonization, becoming alkaline. |
| Skim milk | | |
| | Vegetative Growth: | Brown growth ring |
| | Aerial Mycelium: | None |
| | Soluble Pigment: | Brown |
| | Coagulation and/or peptonization: | Peptonization, becoming alkaline. |
| Potato plug | | |
| | Vegetative Growth: | Dark brown |
| | Aerial Mycelium: | None |
| | Soluble Pigment: | Brown |
| Loeffler's Blood serum | | |
| | Vegetative Growth: | Grayish tan |
| | Aerial Mycelium: | None |
| | Soluble Pigment: | None |
| | Liquefaction: | Moderate |
| Nutrient tyrosine agar | | |
| | Vegetative Growth: | Reverse - very dark brown |
| | Aerial Mycelium: | Moderate - grayish |
| | Soluble Pigment: | Dark brown |
| | Decomposition of tyrosine: | Yes |
| Carbon utilization | | |
| | Pridham-Gottlieb basal medium + 1% carbon source; + = growth; ± = growth poor or questionable; — = no growth as compared to negative control (no carbon source). | |
| | Glucose | + |
| | Arabinose | + |
| | Cellulose | — |
| | Fructose | + |
| | Inositol | + |
| | Lactose | + |
| | Maltose | + |
| | Mannitol | + |
| | Mannose | + |
| | Raffinose | + |
| | Rhamnose | + |
| | Sucrose | + |
| | Xylose | + |
| Temperature range | (Yeast extract-dextrose + salts agar) | |
| 28° C. | - | Good growth for vegetative and aerial mycelia. |
| 37° C. | - | Good growth for vegetative and aerial mycelia. |
| 50° C. | - | Moderate vegetative growth - no aerial. |

Oxygen requirement (Stab culture in yeast extract-dextrose + salts agar).
Aerobic
All readings taken after three weeks at 28° C. unless noted otherwise. pH of all media approximately neutral (6.8 – 7.2).
Color number designations taken from Color Harmony Manual, 1958, 4th Edition, Container Corporation of America, Chicago, Ill.

The above description of the microorganism producing Sulfomycin is given as illustrative of the strain of Streptomyces cineroviridis which can be employed in the production of Sulfomycin. However, the present invention also embraces mutant species of the above described microorganism. For example, those mutants which are obtained by natural selection or those produced by mutating agents including X-ray irradiation, ultraviolet irradiation, nitrogen mustards or like treatments are also included within the ambit of this invention.

Sulfomycin is produced during the aerobic fermentation of suitable aqueous nutrient media, under conditions described hereinafter, by a strain of *Streptomyces cineroviridis*. Aqueous media such as those used for the production of other antibiotics are suitable for use in this process for the preparation of Sulfomycin.

Such media contain sources of carbon and nitrogen assimilable by the microorganism and inorganic salts. In addition, the fermentation media may contain traces of metals necessary for the growth of the microorganisms which are usually present in complex sources of carbon and nitrogen of the medium.

In general, carbohydrates such as sugars, for example dextrose, sucrose, maltose, lactose, dextran and the like, and starches are suitable sources of assimilable carbon in the nutrient media. The exact quantity of the carbon source which is utilized in the medium will depend, in part, upon the other ingredients in the medium but it is usually found that the amount of carbohydrate between about 0.5 and 5% by weight of the medium is satisfactory. These carbon sources can be used individually or several such carbon sources may be combined in the medium.

Various nitrogen sources such as yeast hydrolysates, yeast autolysate, soybean meal, caesin hydrolysates, corn steep liquors, distillers solubles, meat extract and the like, are readily assimilable by the new strain of *Streptomyces cineroviridis* in the production of Sulfomycin. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, ammonium, calcium, phosphate, sulfate, chloride, carbonate and like ions. Also included are trace metals such as cobalt, manganese, iron and magnesium.

It should be noted that the media described in the Examples are merely illustrative of the wide variety of media which may be employed, and are not intended to be limitative.

The following are Examples of media suitable for growing strains of *Streptomyces cineroviridis* for producing Sulfomycin:

| Medium No. 1 | |
|---|---|
| Corn Steep Liquor | 15.0 g/l |
| Distiller's Solubles | 15.0 g/l |
| Glycerol | 10.0 g/l |
| Pharmamedia Cottonseed Meal | 10.0 g/l |
| (Available from Traders Protein Div. of Traders Oil Mill Co., Fort Worth, Texas) | |
| $CaCO_3$ | 3.0 g/l |
| Polyglycol P2000 | 2.5 ml/l |
| $CoCl_2 \cdot 6H_2O$ | 0.01 g |
| Distilled Water | 1000 ml |
| pH 7.3 | |
| Medium No. 2 | |
| Tomato Paste | 20.0 g/l |
| CPC Industrial Starch Modified | 20.0 g/l |
| (Available from CPC Industrial Inc., Industrial Div., Engelwood Cliffs, N.J.) | |
| Primary Yeast | 10.0 g/l |
| $CoCl_2 \cdot 6H_2O$ | 0.005 g/l |
| Distilled Water | 1000 ml |
| pH 7.2–7.4 | |
| Medium No. 3 | |
| Cerelose | 20.0 g/l |
| Pharmamedia Cottonseed Meal | 8.0 g/l |
| Corn Steep Liquor | 5.0 g/l |
| Distilled Water | 1000 ml |
| pH 7.0 | |
| Medium No. 4 | |
| Oat Flour | 20.0 g/l |
| Tomato Paste | 20.0 g/l |
| Distilled Water | 1000 ml |

-continued

| | |
|---|---|
| pH 5.5 | |

The fermentation employing the Sulfomycin producing microorganisms can be conducted at temperatures ranging from about 20° to about 40° C. For optimum results, it is most convenient to conduct these fermentations at a temperature in the range of from about 24° to about 30° C. Temperatures of about 27°–28° C. are most preferred. The pH of the nutrient medium suitable for producing Sulfomycin can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a sulfomycin producing strain of *Streptomyces cineroviridis* loosely stopping the necks of the flask with cotton and permitting the fermentation to proceed in a constant room temperature of about 28° C. on a shaker for about 3 to 10 days. For larger scale work, it is preferable to conduct the fermentation in suitable tanks provided with an aqitation and a means of aerating the fermentation medium. The nutrient medium is made up in the tank and after sterilization is inoculated with a suitable source of vegetative cellular growth of a Sulfomycin producing strain of *Streptomyces cineroviridis*. The fermentation is allowed to continue for from 1 to 5 days while agitating and/or aerating the nutrient medium at a temperature in the range of from about 24° to 37° C.

The Examples which follow are illustrative of the fermentation processes useful in the production of Sulfomycin:

EXAMPLE 1

A lyophilized tube of a culture of *Streptomyces cineroviridis* NRRL-8155 is opened aseptically and the contents suspended in 0.8 ml. sterile Davis salts solution composed of the following:

| Sodium citrate | 0.5 g. |
|---|---|
| $K_2HPO_4$ | 7.0 g. |
| $KH_2PO_4$ | 3.0 g. |
| $(NH_4)_2SO_4$ | 1.0 g. |
| $MgSO_4 \cdot 7H_2O$ | 0.1 g. |
| Distilled water | 1000 ml. |

This suspension is used to inoculate 9 slants of a medium identified as Medium No. 5:

| Corn meal | 20.0 g. |
|---|---|
| Soybean meal | 15.0 g. |
| Distillers solubles | 10.0 g. |
| Sodium citrate | 4.0 g. |
| $CaCl_2 \cdot 2H_2O$ | 0.5 g. |
| $MgSO_4 \cdot 7H_2O$ | 0.1 g. |
| $CoCl_2 \cdot 6H_2O$ | 0.01 g. |
| $FeSO_4 \cdot 7H_2O$ | 0.01 g. |
| Polyglycol P2000 | 2.5 ml. |
| Agar | 20.0 g. |
| Distilled water | 1000.0 ml. |
| pH 6.5 | |

The inoculated slants are incubated for 7–10 days at 27°–28° C. in the dark. The slants are then stored at 4°–6° C. until used to inoculate seed flasks. Onehalf of the slants are used to inoculate 3 baffled 250 ml. Erlemmeyer flasks containing 50 ml. of a medium identified as Medium No. 6:

| | |
|---|---|
| Soluble starch | 10.0 g. |
| Ardamine pH | 5.0 g. |
| (Autolyzed yeast extract powder available from Yeast Products Inc., Paterson, N.J.) | |
| NZ Amine E | 5.0 g. |
| (Enzymatic digest of casein available from Sheffield Chemical, an operation of Kraftco Corp., 2400 Morris Ave., Union, N.J.) | |
| Beef extract | 3.0 g. |
| Cerelose | 1.0 g. |
| $KH_2PO_4$ | 0.182 g. |
| $Na_2HPO_4$ | 0.190 g. |
| $MgSO_4 \cdot 7H_2O$ | 0.05 g. |
| $CaCO_3$ | 0.5 g. |
| Distilled water | 1000.0 ml. |
| pH 7.0–7.2 | |

The seed flasks are shaken for two days at 27°–28° C. on a 220 RPM shaker (2 inch throw). The contents of these flasks are pooled and used to inoculate 20 × 250 ml. unbaffled Erlemmeyer production flasks (2 ml. of inoculum in each) containing 40 ml. of a production medium identified as Medium No. 7:

| | |
|---|---|
| Corn meal | 20.0 g. |
| Soybean meal | 15.0 g. |
| Distillers solubles | 10.0 g. |
| $CaCO_3$ | 4.0 g. |
| $CaCl_2 \cdot 2H_2O$ | 0.5 g. |
| $MgSO_4 \cdot 7H_2O$ | 0.1 g. |
| $CoCl_2 \cdot 6H_2O$ | 0.01 g. |
| $FeSO_4 \cdot 7H_2O$ | 0.01 g. |
| Polyglycol P2000 | 2.5 ml. |
| Distilled water | 1000 ml. |
| pH 6.5 | |

After inoculation, the production flasks are inoculated at 27°–28° C. with agitation on a 220 RPM shaker (2 inch throw) for from 2 days and 5 hours to 3 days. At the end of this period the flasks are harvested and assayed for activity by using standard assay techniques.

EXAMPLE 2

A lyophilized tube of a culture of *Streptomyces cineroviridis* NRRL-8155 is opened aseptically and the contents suspended in 0.8 ml. sterile Davis salts solution. A portion of this suspension is used to inoculate 4 slants of a medium identified as Medium No. 8:

| | |
|---|---|
| Glycerol | 10.0 g. |
| Asparagine | 1.0 g. |
| NZ Amine E | 0.5 g. |
| Ardamine pH | 0.5 g. |
| $K_2HPO_4$ | 1.0 g. |
| Vitamin B | 0.001 g. |
| Agar (Bacto) | 20.0 g. |
| Distilled water | 1000.0 ml. |
| pH 7.2 | |

The inoculated slants are incubated for 7–10 days at 27°–28° C. in the dark. The slant is then stored at 4°–6° C. until to inoculate seed flasks.

The inoculated slants are used as described in Example 1 for the preparation of 250 ml. production flasks containing Sulfomycin. The production flasks of Examples 1 and 2 may be used to inoculate still larger vessels of fermentation medium or they may be combined in order to isolate the Sulfomycin as described in Example 4.

EXAMPLE 3

10 Ml. of the medium from the production flasks is used to inoculate 500 ml. of Medium No. 6 in a 2 liter baffled Ehrlemmeyer flask. The inoculated medium is incubated on a rotary shaker (2 inch throw) at 28° C. for 2 days.

The contents of the 2 liter Ehrlemmeyer flask are used to inoculate 160 liters of a modified Medium No. 6 (in which the soluble starch is replaced by an equal amount of CPC Industrial starch modified) in a 189 liter stainless steel fermentor equipped with an agitator and an aerator. The inoculated medium is incubated for 2 days at 28° C. with agitation at 150 revolutions per minute and aerations at 3 cubic feet per minute.

The contents of the 189 liter fermentor may be treated as in Example 4 to recover the produced antibiotic or 40 liters thereof may be employed to inoculate 467 liters of Medium No. 7 in a 756 liter stainless steel fermentor equipped with an agitator and an aerator. The medium is incubated at 28° C. for 2 days with agitation at 130 revolutions per minute and aeration at 10 cubic feet per minute.

EXAMPLE 4

A. 400 Liters of fermentation broth of Example 3C is filtered and the filter (mycelial) cake washed with water. The mycelial cake is stirred twice with 200 liters of acetone for ½ hour and filtered. The acetone filtrates are combined and evaporated into 200 liters of water at pH 7.0 under vacuum at less than 30° C. (That is, as the acetone is evaporated, 200 liters of water is added to the filtrates).

The water layer is extracted twice with 200 liters of ethyl acetate and the extracts are combined. The ethyl acetate is dried and evaporated to an oily residue. The oil is treated with 4 liters of hexane and the resulting precipitate filtered and washed with benzene.

The solid material is dissolved in 375 ml. of chloroform and passed through a column of silica gel eluting with chloroform containing progressively from 4–16% methanol. Most of the antibiotic is removed with 8% methanol.

The major active fractions are evaporated into 100 ml. of methanol with a resultant precipitation. The methanol insoluble portion is dried and weighs 0.436 g. The methanol filtrate is evaporated recovering 1.84 g. of solids. Both materials had the same specific bioactivity and are 62% pure Sulfomycin.

Alternatively, in order to obtain pure material, the initial solid material obtained from the hexane precipitation is further washed with ethyl ether in order to obtain a dry solid material weighing 9.04 g. which assays as 51% pure.

Five grams of the solid material is dissolved in 450 ml. of chloroform and is passed through 350 g. of silica gel, eluting first with 1,400 ml. of 4% methanol in chloroform to remove impurities followed by 7 × 400 ml. fractions of 6% methanol in chloroform. The major bioactivity is found in fractions 3 and 4 and these fractions are precipitated with ethyl ether to yield 518 and 485 mg. of solids respectively.

180 mg. of the fourth fraction is dissolved in 10 ml. of warm methanol which is cooled yielding 28 mg. of insoluble material. The methanol solution is treated with ethyl ether to yield 126 mg. of pure Sulfomycin I.

This sample is compared with an authentic sample of Sulfomycin I, and found to be identical by Nuclear Magnetic Resonance thin Layer Chromatography on silica gel plates and UV absorption.

What is claimed is:

1. A process for the preparation of Sulfomycin I which comprises fermenting with a Sulfomycin I producing strain of Streptomyces cineroviridis, NRRl 8155 and mutants thereof an aqueous nutrient medium containing an assimilable source of carbon, an assimilable source of nitrogen and inorganic salts under aerobic conditions.

2. The process of claim 1 wherein the fermentation is conducted at a temperature of from about 20° to 40° C. and a pH of from about 5.0 to 9.0.

3. The process of claim 2 wherein the temperature is from about 24 to 30° C. and the pH is from about 6.0 to 7.5.

4. The process of claim 3 wherein the temperature is about 27 to 28° C.

5. The process of claim 1 wherein the nutrient medium contains carbohydrate sources of from 0.5 to 5% by weight and nitrogen sources of from 0.2 to 6% by weight.

6. The process of claim 1 wherein the fermentation is complete in from about 1 to 5 days.

7. The process of claim 1 wherein the Sulfomycin is isolated.

8. The process of claim 1 wherein the Sulfomycin I producing strain is *Streptomyces cineroviridis* NRRL-8155.

9. A process for ther preparation of Sulfomycin I which comprises fermenting with a Sulfomycin I producing strain of *Streptomyces cineroviridis*, NRRL 8155 and mutants thereof an aqueous nutrient medium containing an assimilable source of carbon, an assimilable source of nitrogen and inorganic salts under aerobic conditions, and isolating Sulfomycin I from the fermentation medium.

* * * * *